United States Patent [19]

Wischniewski et al.

[11] 4,313,930

[45] Feb. 2, 1982

[54] STABLE VALEPOTRIATE COMPOUNDS AND PROCESS FOR THEIR PREPARATION

[75] Inventors: Martin Wischniewski; Lutz Feicho, both of Neustadt; Werner Althaus, Burgdorf, all of Fed. Rep. of Germany

[73] Assignee: Kali-Chemie Pharma GmbH, Hanover, Fed. Rep. of Germany

[21] Appl. No.: 89,718

[22] Filed: Oct. 31, 1979

[30] Foreign Application Priority Data

Nov. 11, 1978 [DE] Fed. Rep. of Germany ....... 2849029

[51] Int. Cl.³ .......................... A61K 9/32; A61K 9/34; A61K 9/36; A61K 31/35
[52] U.S. Cl. ........................................ 424/32; 424/31; 424/33; 424/34; 424/35; 424/283; 424/361; 424/195; 264/4

[58] Field of Search ................... 424/35, 31, 283, 361, 424/195, 32, 33, 34; 264/4

[56] References Cited

U.S. PATENT DOCUMENTS 3,869,476 3/1975 Thies et al. ......................... 424/283

FOREIGN PATENT DOCUMENTS 2230626 1/1974 Fed. Rep. of Germany ...... 424/195

Primary Examiner—Donald B. Moyer
Attorney, Agent, or Firm—Schwartz, Jeffery, Schwaab, Mack, Blumenthal & Koch

[57] ABSTRACT

Stable valepotriate compositions are produced by a process wherein impurities are removed from the pharmaceutically active extract of the valerianacea fruits, followed by a mixing with pharmaceutically acceptable sheathing materials and the formation of microspheres therefrom.

10 Claims, No Drawings

STABLE VALEPOTRIATE COMPOUNDS AND PROCESS FOR THEIR PREPARATION

BACKGROUND OF THE INVENTION

The invention relates to stable valepotriate preparations and process for their production.

Valepotriates designate a group of therapeutically valuable substances which may be obtained from the roots and rhizomes of various valerianacea and kentranthus species. The most important representatives of the valepotriates are valtratum, isovaltratum, didrovaltratum and acevaltratum. They may be extracted from the dried drug in amounts of up to approximately 5%. The proportions of the individual valepotriates with respect to each other vary in accordance with the origin of the substance. For example, didrovaltratum predominates in valepotriates of Asian origin and valtratum and isovaltratum predominates in valepotriates of European or Mexican origin. Acevaltratum, on the other hand, is always present in less significant proportions.

Valepotriates are extremely sensitive substances and are rapidly decomposed by the effects of heat, light and chemial agents, and even of moisture though they are practically insoluble in water. Valepotriates cannot be, therefore, maintained in the stable condition under normal storage conditions for an adequate period of time, either in the drug form or in the isolated form.

Because of these difficulties, there have been attempts to prepare valepotriates in a form that would remain stable over a longer period of time.

One such attempt, West German Published application No. 22 30 626, describes a valerian product produced by means of the dissolution of a valerianacea extract in a multivalent alcohol, a fatty oil or an ethereal oil or mixtures thereof. This product purportedly exhibits no appreciable decomposition phenomena after storage for five months at room temperature. In storage at temperatures below 10° C., the solution described is claimed to remain stable for at least 12 months. Without an indication of the details of its effects on the stability, microencapsulation of the above-described solution is also mentioned. The stability of 5 to 12 months observed therein does not represent an adequate period of time for finished medicinal forms. Investigations extending over longer periods of time reveal the onset of decomposition phenomena even in preparations of this type.

A further attempt to stabilize valerian extracts is found in West German Offenlegungsschrift No. 26 54 709 wherein preparations dehydrated to a residual water content of less than 0.5% is described. This proposal requires additional, in part extreme measures, such as for example working under nitrogen. Observations up to about 6 months demonstrate that preparations of this type attain only moderate stability.

SUMMARY OF THE INVENTION

It is, therefore, an object of the invention to provide valepotriate preparations which are stable over periods of time considered desirable for pharmaceutical preparations. At the same time, the valepotriate preparations of this invention avoid the disadvantages inherent in the state of the art.

These objects and advantages are achieved by a process for the preparation of stable valepotriate compositions comprising removing non-specific impurities from a pharmaceutically active valerianacea extract to produce a purified valepotriate fraction, mixing the purified valepotriate fraction with an aqueous solution of a material capable of producing a pharmaceutically acceptable sheathing for a pharmaceutically active material, and forming microspheres from the mixture of purified valepotriate fraction and sheathing material. In the final valepotriate composition the microspheric form is stable for prolonged periods of time and contains from about 2% to about 40% by weight of a pharmaceutically active ingredient.

The invention attains this object by forming of microspheric encapsulation of water soluble, physiologically indifferent and pharmaceutically acceptable sheathing materials and valerianacea extracts freed essentially from undesirable accompanying substances.

These preparations surprisingly exhibit no decline in stability over periods of observation. Even for periods of one to three years, the preparations remain surprisingly stable without any extreme precautionary measures being observed. The preparations have a water content of approximately 3% (as determined by the method of Karl Fischer) and are present in the form of a pourable powder of microcapsules. The microencapsulated valepotriate preparations according to the invention transform the liquid or semisolid active ingredient into a dry powder, readily processable technically to the various galenic forms. The processing also coats the highly odor-sensitive valepotriates. It is not necessary to store them with cooling, as is required for the pure valepotriates or the known solutions.

It has been discovered, however that it is extremely important that the extract used be essentially free of non-specific accompanying substances to provide the improved stability. This is accomplished by extracting the powdered drugs with low boiling lipophilic solvents at temperatures less than approximately 30° C. and removing the solvent under vacuum again at temperatures less than approximately 30° C. It is of advantage in the extraction to maintain a weakly acidic pH to the extent that the extraction mixture does not by itself display the abovementioned pH value as the result of acidic accompanying substances. The pH may then be adjusted by means of the addition of acidic substances. The raw extract obtained in this manner is dissolved in 90% acetic acid. The non-specific accompanying substances are subsequently extracted from the mixture of the raw extract and acetic acid, with gasoline or a similar solvent immiscible with water. The valepotriates are then concentrated out from the residual acetic acid phase after dilution with water to a volume of 1.5 to 2 times with low boiling lipophilic solvents immiscible with water. Following the removal of the solvent under vacuum, the valepotriates are obtained, depending on the origin of the drug, in the form of oily to semisolid, lardaceous masses resembling in appearance partially crystallized honey with their own odor, free of the specific odor of isovalerianic acid. This mass will be designated hereinafter as the "purified" or "genuine valepotriate fraction". It contains roughly 80% by weight valepotriate. A more detailed description of preferred procedures employed in obtaining the purified valepotriate fraction is found in U.S. Pat. Nos. 3,422,090 and 3,869,476. The descriptive portions of these patents are incorporated herein by reference.

The sheathing materials, aside from the fact that they must be soluble in water and physiologically neutral, are not required to satisfy any special conditions. The substances that may be considered are those customarily used for the microencapsulation of medications, preferably gum arabic, methylcellulose or mixed polymers of polyvinyl pyrrolidone and polyvinyl acetate.

In the production of the preparations according to the invention, the sheathing material, possibly with heating, is dissolved in water and intensively mixed with the genuine valepotriate fraction and the mixture processed into microcapsules. In a preferred embodiment, the genuine valepotriate fraction is preheated prior to mixing. The microencapsulation may be effected in the conventional manner, by spray drying, for example.

For the aqueous solutions of the sheathing materials, concentrations between 35 parts by weight sheathing materials and 65 parts by weight of water and 2.5 parts by weight sheathing materials and 97.5 parts by weight water are suitable. The ranges are determined by the fact that excessively concentrated and consequently viscous solutions cannot be spray dried, while overly dilute solutions are not economical in the spray drying process. The ratio of the genuine valepotriate fraction by the sheathing material may vary between 50:50 parts by weight and 2.5:97.5 parts by weight. Extract concentrations higher than 50% by weight (with respect to the finished microcapsule) are possible but do not yield dry, flowable powders, while the lower limit of 2.5% by weight is determined by aspects of dosage. With the above-mentioned content of 80% by weight of valepotriates in the genuine valepotriate fraction, concentrations are achieved in the final product corresponding to a content of active ingredients in the microcapsules of between 40 and 2% by weight.

EXAMPLES

Three different stable valepotriate products are prepared. Genuine valepotriate fraction is prepared, according to the procedures of U.S. Pat. No. 3,422,090, from the raw drug of plants from the genus Valeriana and is mixed with various substances for the microencapsulation procedure. In Example 1, gum arabic and methylcellulose are employed as the microencapsulation adjuvant. In Example 2, gum arabic, methylcellulose and a mixed polymer of polyvinylpyrrolidone and polyvinylacetate is employed. In Example 3, gum arabic and a mixed polymer of polyvinylpyrrolidone and polyvinylacetate forms the microencapsulation adjuvant. The mixed polymer of polyvinylpyrrolidone and polyvinylacetate is a commercially available product known as Luviskol VA64 available from BASF comprising six parts polyvinylpyrrolidone, four parts polyvinylacetate. In each of the examples, the respective aqueous solutions of gum arabic, methylcellulose and Luviskol are mixed and heated at 40° C. The molten genuine valepotriate fraction, also heated at 40° C. is added under intensive agitation to the solution of the sheathing materials. In the case of Example 3, another 18.0 kg water are added to the solution. The mixture is homogenized by means of a colloid gear mill (Puc-Viscosator). The emulsion obtained is immediately thereafter spray dried in centrifugal atomizing dryer (Krause tower).

The valepotriate in each example is determined by means of the so-called expoxy method. In the process, approximately 200 mg of the substance is exactly measured into a tall 50 ml beaker and mixed with 500 mg tetraethylammonium iodide. Following the addition of 30 ml of a mixture of 50 parts chloroform, 30 parts glacial acetic acid and 20 parts acetic anhydride, the mixture is heated in 25 minutes to 65° C. on an electrically heated magnetic agitator in a graphite bath. The bath should already be at the temperature specified when the beaker is placed on it. The beaker is covered with a watch glass.

After exactly 25 minutes, the reaction mixture is titrated while still warm with 0.1 N perchloric acid by means of a metrohm-potentiograph. A combination glass electrode adjusted to a ph range of 14 is used.

The calculation of the valepotriate content is effected by the following formula:

$$\frac{\text{ml HClO}_4 \text{ consumed} \times 42.5 \times 100}{\text{amounts weighed in}} = \% \text{ valepotriate}$$

TABLE

| | Example 1 | Example 2 | Example 3 |
|---|---|---|---|
| Gum Arabic | 3.0 kg | 3.0 kg | 2.5 kg |
| Water | 6.0 kg | 6.0 kg | 5.0 kg |
| Methylcellulose 25 cps | 2.0 kg | 2.0 kg | — |
| Water | 28 kg | 22.0 kg | — |
| Luviskol VA 64 | — | 1.0 kg | 5.0 kg |
| Water | — | 5.0 kg | 18.0 kg |
| Genuine Valepotriate Fraction | 5.0 kg | 5.0 kg | 2.5 kg |
| Initial % Valepotriate Immediately After Preparation | 39.9 | 38.0 | 20.15 |
| % Valepotriate at 11 months | 39.9 | 38.9 | — |
| % Valepotriate at 36 months | — | — | 22.0 |

What is claimed is:

1. A process for the preparation of a stable valepotriate composition comprising removing non-specific impurities from a pharmaceutically active valerianacea extract to produce a purified valepotriate fraction, mixing said purified valepotriate fraction with an aqueous solution containing at least one pharmaceutically acceptable sheathing compound, and forming microspheres from said mixture of sheathing compound and purified valepotriate fraction.

2. A process for the preparation of a stable valepotriate composition according to claim 1 wherein said mixture is subjected to a microencapsulation process to form said microspheres.

3. The process of claim 2 wherein said microencapsulation process is effected by spray drying said mixture.

4. The process of claim 1 wherein said removing of non-specific impurities comprises extracting pharmaceutically active valerianacea drug in powdered form with low boiling lipophilic solvents at a temperature of less than 30° C., adjusting the extraction mixture to a weakly acid pH, removing said solvents under vacuum at a temperature of less than 30° C. to produce a raw extract, dissolving said raw extract in a carboxylic acid removing said impurities from said carboxylic acid solution and recovering the purified valerianacea extract from said purified carboxylic acid solution.

5. The process of claim 1 wherein said aqueous solution contains from about 2.5 to about 50% by weight of purified valepotriate fraction.

6. The process of claim 1 wherein said pharmaceutically acceptable sheathing compound is selected from the group consisting of gum arabic, methyl-cellulose and mixed polymers of polyvinylpyrrolidone and polyvinyl acetate.

7. The process of claim 6 wherein said sheathing compound is mixed with water in a ratio of from 35:65 to 2.5:97.5.

8. A valepotriate preparation comprising a purified valerianacea extract and a pharmaceutically acceptable sheathing material in the form of microcapsules.

9. the valepotriate preparation of claim 8 wherein the pharmaceutically acceptable sheathing material is selected from the group consisting of gum arabic, methylcellulose and mixed polymers of polyvinylpyrrolidone and polyvinylacetate.

10. The valepotriate preparation of claim 8 wherein said purified valerianacea extract is present in an amount of from about 2.5 to about 50% by weight.

* * * * *